United States Patent [19]

Grollier

[11] Patent Number: 4,591,610

[45] Date of Patent: May 27, 1986

[54] THICKENED OR GELLED COMPOSITION FOR CONDITIONING HAIR

[75] Inventor: Jean F. Grollier, Paris, France

[73] Assignee: L'Oreal, Paris, France

[21] Appl. No.: 592,934

[22] Filed: Mar. 23, 1984

[30] Foreign Application Priority Data

Mar. 23, 1983 [LU] Luxembourg .............................. 84708

[51] Int. Cl.$^4$ .............................................. A45D 7/00
[52] U.S. Cl. .......................................... 524/55; 132/7; 424/70
[58] Field of Search ............................ 424/70; 524/55

[56] References Cited

U.S. PATENT DOCUMENTS

| | | | |
|---|---|---|---|
| 3,467,647 | 9/1969 | Benninga | 524/55 |
| 3,658,734 | 4/1972 | Pettitt | 524/55 |
| 3,868,340 | 2/1975 | Keegan | 524/55 |
| 3,947,396 | 3/1976 | Kangas | 524/521 |
| 4,061,602 | 12/1977 | Oberstar | 424/70 |
| 4,143,007 | 3/1979 | DeMartino | 524/55 |
| 4,240,450 | 12/1980 | Grollier | 132/7 |
| 4,356,819 | 11/1982 | Potaczek | 524/55 |
| 4,445,521 | 5/1984 | Grollier | 132/7 |

FOREIGN PATENT DOCUMENTS

| | | |
|---|---|---|
| 2225462 | 11/1974 | France . |
| 2383660 | 10/1978 | France . |
| 7104188 | 10/1972 | Netherlands . |
| 2098624 | 11/1982 | United Kingdom . |

OTHER PUBLICATIONS

Chemical Abstracts, vol. 98, No. 12, Mar. 21, 1983, p. 362.

Primary Examiner—Paul R. Michl
Attorney, Agent, or Firm—Fleit, Jacobson, Cohn & Price

[57] ABSTRACT

The invention provides a composition suitable for application to the hair which is in the form of a thickened, stable and homogeneous lotion containing either at least one cationic polymer and at least one anionic or amphoteric polymer or at least one anionic polymer and at least one cationic or amphoteric polymer and at least one xanthan gum.

21 Claims, No Drawings

THICKENED OR GELLED COMPOSITION FOR CONDITIONING HAIR

The present invention provides a thickened, stable and homogeneous composition for conditioning hair, which contains either at least one cationic polymer, and at least one anionic or amphoteric polymer or at least one anionic polymer and at least cationic or amphoteric polymer and at least one xanthan gum and a process for conditioning hair using these compositions.

The Applicant Company has already described and claimed, in French Pat. No. 2,383,660, compositions based on cationic polymers and anionic polymers for the treatment of hair.

These compositions enable moistened hair to be combed easily, give the hair a pleasant feel and enable a shine, hold and volume to be achieved on dry hair.

Since the use of these compositions is by a process comprising application of the composition with a residence time in contact with the hair and rinsing thereof, it is generally advisable to use compositions which stay on the hair well, that is to say which do not run. This is the form generally advisable for so-called rinsing compositions or "rinses".

The Applicant Company has studied various thickeners, and in particular vegetable thickeners, for example alginates, carrageenates, gum arabic and cellulose derivatives, such as methylcellulose, hydroxymethylcellulose, hydroxyethylcellulose, hydroxypropylcellulose, hydroxypropylmethylcellulose and carboxymethylcellulose. Such compositions frequently have the disadvantage that they are relatively unstable on storage. In fact, it has been found that decantation may result, if the re-solution of the thickeners is not complete, in cosmetic properties far inferior to those which would be expected of the composition initially prepared.

We have not discovered, according to the present invention, that the addition of xanthan gums to compositions which are based on cationic polymers and anionic polymers provides compositions having a far better stability and homogeneity than compositions previously provided.

The xanthan gums used according to the present invention are known per se and are polysaccharides which can be synthesised by fermentation of certain sugars by microorganisms, such as the bacterium Xanthomonas campestris.

These gums generally have a molecular weight of from 1 million to 50 million and a viscosity of from 850 to 1,600 cps for an aqueous composition containing 1% of xanthan gum (measured on a viscometer of the Brookfield LVF type, at 60 revolutions/minute).

Gums which are more particularly preferred according to the invention are commercial products, such as Keltrol, marketed by Kelco, Rhodopol 23 C, marketed by Rhône-Poulenc, Actigum CX 9, marketed by Ceca, and Deuteron XG, marketed by Schöner.

We have found that the cosmetic properties imparted by the association of a cationic polymer and an anionic polymer are in no way modified by the presence of xanthan gum; on the contrary, these characteristics were improved in that these polymers are kept in contact with the hair in a uniform manner.

The compositions according to the invention may also contain cationic, anionic, non-ionic or amphoteric surface-active agents or mixtures thereof.

In one of the preferred embodiments, the compositions contain electrolytes, such as alkali metal salts, such as sodium, potassium or lithium salts, these salts preferably being the halides, such as the chloride or bromide, the sulphates or the organic acid salts, such as the acetates or lactates. Electrolytes which can also be used according to the invention are the alkaline earth metal salts, preferably carbonates, silicates, nitrates, acetates, gluconates, pantothenates and lactates of calcium, magnesium and strontium.

The preferred electrolyte is sodium chloride.

The cationic and anionic polymers are generally present in the compositions according to the invention in amounts of from 0.01 to 10% by weight, preferably from 0.05 to 5% by weight, based on the total weight of the composition. The weight ratio of cationic polymers to anionic polymers in general varies from 0.1:1 to 40:1, preferably from 0.1:1 to 5:1.

The xanthan gums used in the compositions according to the invention are generally present in amounts of from 0.05 to 5% by weight, preferably from 0.1 to 1% by weight, based on the total weight of the composition.

The cationic, anionic, non-ionic and amphoteric surface-active agents or mixtures thereof are in general used in amounts of from 0.1 to 70% by weight, preferably from 0.5 to 50%, based on the total weight of the composition.

The cationic polymers used according to the invention are generally polymers of the polyamine, polyaminopolyamide or quaternary polyammonium type, in which the amine or ammonium grouping is part of the polymer chain or is bonded thereto, and they have a molecular weight of from 500 to 3,000,000.

The anionic polymers are generally polymers which have a molecular weight of from 500 to 3,000,000 and contain carboxylic and/or sulphonic groups.

The cationic polymers which can be used according to the invention are generally chosen from the following polymers:

(1) Copolymers of vinylpyrrolidone and dialkylaminoalkyl acrylate or methacrylate (quaternised or non-quaternised), such as those marketed under the names Gafquat, by the Gaf Corp., for example, "copolymer 845", and "Gafquat 734 or 755", which are described in French Pat. No. 2,077,143 and French Pat. No. 2,393,573.

(2) Cellulose ether derivatives which contain quaternary ammonium groupings, such as those described in French Pat. No. 1,492,597, and in particular the polymers marketed under the names JR, such as JR 125, JR 400 and JR 30 M, and LR, such as LR 400 and LR 30 M, by Union Carbide Corp., and cationic cellulose derivatives, such as CELQUAT L 200 and CELQUAT H 100, marketed by National Starch and described in U.S. Pat. No. 4,131,576.

(3) Cationic polysaccharides, such as those described in U.S. Pat. Nos. 3,589,978 and 4,031,307, and in particular Juguar C. 13 S, marketed by Meyhall.

(4) Cationic polymers chosen from:

(a) polymers containing units of the formula: —A—Z—A—Z—(I) in which A represents a radical containing two amine functions, preferably piperazinyl, and Z represents the symbol B or B'; and B and B' are identical or different and represent a bivalent radical which is a straight-chain or branched alkylene radical which contains up to 7 consecutive carbon atoms in the principal chain, is unsubstituted or substituted by hydroxyl groupings and may also contain oxygen, nitrogen and/or sulphur atoms and 1 to 3 aromatic and/or heterocyclic rings; the oxygen, nitrogen and sulphur atoms being in the form of ether, thioether, sulphoxide, sulphone, sulphonium, amine, alkylamine, alkenylamine, benzylamine, amine oxide, quaternary ammonium, amide, imide, alcohol, ester and/or urethane groupings; these polymers and the process for their preparation are described in French Pat. No. 2,162,025, (b) polymers containing units of the formula: —A—$Z_1$—A—$Z_1$—(II) in which A represents a radical which contains two amine functions, preferably piperazinyl, and $Z_1$ represents the symbol $B_1$ or $B'_1$, at least one of the symbols $Z_1$ signifying the symbol $B'_1$; $B_1$ represents a bivalent radical which is a straight or branched-chain alkylene or hydroxyalkylene radical having up to 7 consecutive carbon atoms in the principal chain, and $B'_1$ represents a bivalent radical which is a straight-chain or branched alkylene radical which has up to 7 consecutive carbon atoms in the principal chain, is unsubstituted or substituted by one or more hydroxyl radicals and is interrupted by one or more nitrogen atoms, the nitrogen atom being substituted by an alkyl chain optionally interrupted by an oxygen atom and optionally containing one or more hydroxyl functions; these polymers and the process for their preparation are described in French Pat. No. 2,280,361, and (c) alkylation products with alkyl or benzyl halides or a lower alkyl tosylate or mesylate and the oxidation products of polymers of the formula (I) or (II)

(5) Optionally alkylated crosslinked polyaminopolyamides chosen from at least one water-soluble crosslinked polymer obtained by crosslinking a polyaminopolyamide (A) prepared by polycondensation of an acid compound with a polyamine. The acid compound is chosen from: (i) organic dicarboxylic acids, (ii) aliphatic monocarboxylic and dicarboxylic acids with a double bond, (iii) esters of the abovementioned acids, preferably esters of lower alkanols having 1 to 6 carbon atoms, and (iv) mixtures of these compounds. The polyamine is chosen from the bis-primary, mono-secondary and bis-secondary polyalkylene-polyamines; 0 to 40 mol % of this polyamine may be replaced by a bis-primary diamine, preferably ethylenediamine, or a bis-secondary diamine, preferably piperazine, and 0 to 20 mol % may be replaced by hexamethylenediamine. Crosslinking is effected by means of a crosslinking agent (B) chosen from epihalohydrins, diepoxides, dianhydrides, unsaturated anhydrides and bisunsaturated derivatives, in amounts of 0.025 to 0.35 mol of crosslinking agent per amine grouping of the polyaminopolyamide (A). These polymers and their preparation are described in more detail in French Pat. No. 2,252,840.

The optional alkylation may be carried out with glycidol, ethylene oxide, propylene oxide or acrylamide.

The crosslinked and optionally alkylated polyaminopolyamides do not contain reactive groupings, do not have alkylating properties and are chemically stable.

The polyaminopolyamides (A) themselves can also be used according to the invention.

(6) Crosslinked water-soluble polyaminopolyamides obtained by crosslinking a polyaminopolyamide (A) (as defined above) by means of a crosslinking agent chosen from:

(I) compounds chosen from: (1) bis-halohydrins, (2) bis-azetidines, (3) bis-haloacyldiamines and (4) alkyl bis-halides;

(II) oligomers obtained by reacting a compound (a) chosen from (1) bis-halohydrins, (2) bis-azetidines, (3) bis-haloacyldiamines, (4) alkyl bis-halides, (5) epihalohydrins, (6) diepoxides and (7) bis-unsaturated derivatives with a compound (b) which is a bifunctional compound able to react with the compound (a); and (III) the quaternisation product of a compound chosen from the abovementioned compounds (I) and the oligomers (II), which contains one or more tertiary amine groupings which can be completely or partly alkylated with an alkylating agent (c), preferably chosen from methyl and ethyl chloride, bromide, iodide, sulphate, mesylate and tosylate, benzyl chloride, benzyl bromide, ethylene oxide, propylene oxide and glycidol. Crosslinking is effected by means of 0.025 to 0.35 mol, in particular 0.025 to 0.2 mol and more particularly 0.025 to 0.1 mol, of crosslinking agent per amine grouping of the polyaminopolyamide.

These crosslinking agents and these polymers as well as the process for their preparation are described in French Pat. No. 2,368,508.

(7) Polyaminopolyamide derivatives resulting from the condensation of polyalkylene-polyamines with polycarboxylic acids, followed by alkylation with bifunctional agents. Examples are polymers of adipic acid and dialkylaminohydroxyalkyl-dialkylene-triamines, in which the alkyl radical contains 1 to 4 carbon atoms and is preferably methyl, ethyl or propyl, as described in French Pat. No. 1,583,363.

Examples of these derivatives are polymers of adipic acid and dimethylamino-hydroxypropyldiethylenetriamine, marketed under the name Cartarétine F, $F_4$ or $F_8$ by SANDOZ.

(8) Polymers obtained by reacting a polyalkylene-polyamine containing two primary amine groupings and at least one secondary amine grouping with a dicarboxylic acid chosen from diglycolic acid and saturated aliphatic dicarboxylic acids having 3 to 8 carbon atoms. The molar ratio of polyalkylene-polyamine to dicarboxylic acid is from 0.8:1 to 1.4:1; the resulting polyaminopolyamide is reacted with epichlorohydrin in a ratio of mol of epichlorohydrin to secondary amine grouping of the polyaminopolyamide of from 0.5:1 to 1.8:1; these products being mentioned in U.S. Pat. Nos. 3,227,615 and 2,961,347.

Polymers of this type are, in particular, HERCOSETT 57 marketed by Hercules Incorporated and having a viscosity of 30 cps in 10% strength aqueous solution at 25° C.; and PD 170 or DELSETTE 101 marketed by Hercules, in the case of the copolymer of adipic acid and epoxypropyldiethylenetriamine.

(9) Cyclic polymers having a molecular weight of 20,000 to 3,000,000, such as homopolymers containing, as the principal constituent of the chain, units corresponding to the formula (III) or (III'):

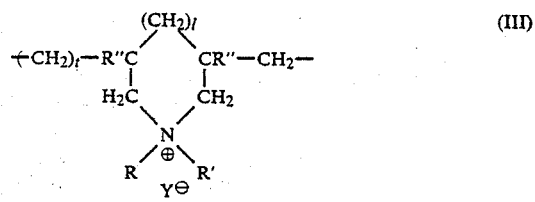

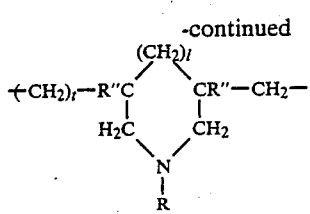

in which L and t are equal to 0 or 1, and the sum of L+t=1, R" represents hydrogen or methyl, R and R' independently represent an alkyl group having 1 to 22 carbon atoms, a hydroxyalkyl group in which the alkyl group preferably has 1 to 5 carbon atoms, or a lower amidoalkyl group or R and R' may designate, together with the nitrogen atom to which they are bonded, heterocyclic groups, such as piperidinyl or morpholinyl, as well as copolymers containing units of the formula (III) or (III') and units derived from acrylamide or diacetone-acrylamide, and $Y^\ominus$ is an anion, such as bromide, chloride, acetate, borate, citrate, tartrate, bisulphate, bisulphite, sulphate or phosphate.

Examples of the quaternary ammonium polymers of the type defined above, are the homopolymer of dimethyl-diallyl-ammonium chloride marketed under the name MERQUAT 100 and having a molecular weight of less than 100,000, and the copolymer of dimethyl-diallyl-ammonium chloride and acrylamide having a molecular weight of greater than 500,000 and marketed under the name MERQUAT 550 by MERCK.

These polymers are described in French Pat. No. 2,080,759 and its Certificate of Addition No. 2,190,406.

(10) Quaternary ammonium polymers containing recurring units of the formula:

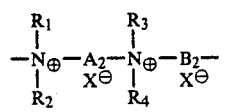

in which $R_1$ and $R_2$, and $R_3$ and $R_4$ are identical or different and represent aliphatic, alicyclic or araliphatic groups containing at most 20 carbon atoms or lower hydroxyaliphatic radicals, or $R_1$ and $R_2$ and $R_3$ and $R_4$, together or separately, form, with the nitrogen atoms to which they are bonded, heterocyclic groups optionally containing a second hetero-atom other than nitrogen, or $R_1$, $R_2$, $R_3$ and $R_4$ represent the group:

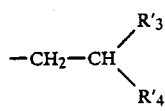

in which $R'_3$ represents hydrogen or lower alkyl and $R'_4$ represents one of the following groups:

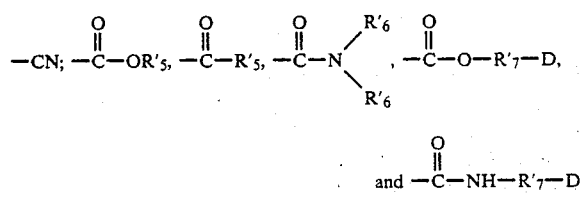

wherein $R'_5$ represents a lower alkyl group, $R'_6$ represents hydrogen or a lower alkyl group, $R'_7$ represents alkylene and D represents a quaternary ammonium group, and $A_2$ and $B_2$ represent polymethylene groups which contain 2 to 20 carbon atoms, may be linear or branched and saturated or unsaturated and may contain, intercalated in the principal chain, one or more aromatic ring(s), such as the groups:

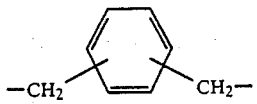

Or:

$$-(CH_2)_n-Y_1-(CH_2)_n-$$

wherein $Y_1$ represents O, S, SO or $SO_2$,

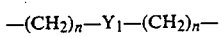

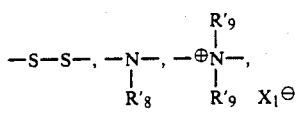

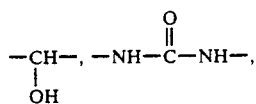

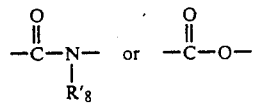

where $X_1^\ominus$ represents an anion derived from an inorganic or organic acid, n is 2 or 3, $R'_8$ represents hydrogen or a lower alkyl group and $R'_9$ represents lower alkyl, or $A_2$ and $R_1$ and $R_3$ represent, with the two nitrogen atoms to which they are bonded, a piperazine ring; in addition, if $A_2$ represents a linear or branched, saturated or unsaturated alkylene or hydroxyalkylene group, $B_2$ may also represent the group:

$$-(CH_2)_n-CO-D-OC-(CH_2)_n-$$

in which D represents:

(a) a glycol radical of the formula $-O-Z-O-$ where Z represents a linear or branched hydrocarbon group or:

or

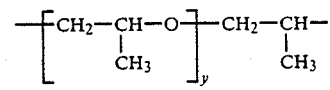

where x and y represent an integer from 1 to 4, representing a defined and single degree of polymerisation, or any number from 1 to 4, representing an average degree of polymerisation;

(b) a radical of a bis-secondary diamine, such as a piperazine derivative;

(c) a bis-primary diamine group of the formula:

$$-NH-Y-NH-$$

where Y represents a linear or branched hydrocarbon radical or the bivalent group $$-CH_2-CH_2-S-S-CH_2-CH_2-;$$

or (d) a ureylene group of the formula $-NH-CO-NH-$; and $X^\ominus$ represents an anion, such as chloride or bromide.

These polymers generally have a molecular weight of from 1,000 to 100,000.

Polymers of this type are described, in particular, in French Pat. Nos. 2,320,330, 2,270,846 and 2,316,271, French Patent Applications 2,336,434 and 2,413,907 and U.S. Pat. Nos. 2,273,780, 2,375,853, 2,388,614, 2,454,547, 3,206,462, 2,261,002 and 2,271,378.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020.

(11) Homopolymers or copolymers derived from acrylic or methacrylic acid containing, as units:

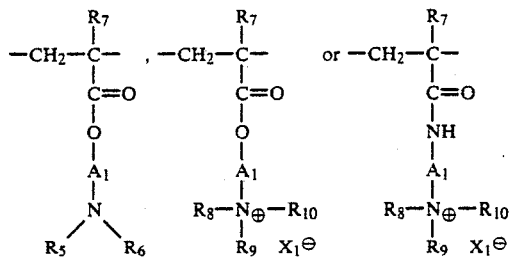

in which $R_7$ represents H or $CH_3$, $A_1$ represents a linear or branched alkyl group with 1 to 6 carbon atoms or a hydroxyalkyl group with 1 to 4 carbon atoms, $R_8$, $R_9$ and $R_{10}$ are identical or different and represent an alkyl group having 1 to 18 carbon atoms or benzyl, $R_5$ and $R_6$ represent hydrogen or an alkyl grouping having 1 to 6 carbon atoms and $X_1^\ominus$ represents a methosulphate or halide anion, such as chloride or bromide.

The comonomer or comonomers which can be used are chosen from: acrylamide, methacrylamide, diacetone-acrylamide, acrylamide and methacrylamide substituted on the nitrogen by lower alkyl radicals, alkyl acrylates and methacrylates, vinylpyrrolidone and vinyl esters.

Examples which may be mentioned are:

the products referred to by the names QUATERNIUM 38, 37, 49 or 42, in the Cosmetic Ingredient Dictionary copolymers of acrylamide and beta-methacryloyloxyethyl-trimethylammonium methosulphate, marketed under the names Reten 205, 210, 220 and 240 by Hercules, the aminoethylacrylate phosphate/acrylate copolymer marketed under the name Catrex by National Starch, which have a viscosity of 700 cps at 25° C. in an 18% strength aqueous solution, and graft and crosslinked cationic copolymers having a molecular weight of 10,000 to 1,000,000, preferably 15,000 to 500,000, which result from copolymerisation of:

(a) at least one cosmetic monomer,
(b) dimethylaminoethyl methacrylate,
(c) polyethylene glycol and
(d) a polyunsaturated crosslinking agent, as described in French Pat. No. 2,189,434.

The crosslinking agent is preferably: ethylene glycol dimethacrylate, diallyl phthalates, divinylbenzenes, tetraallyloxyethane and polyallylsucroses having 2 to 5 allyl groups per mol of sucrose.

The cosmetic monomer can be very varied in type, for example a vinyl ester of an acid having 2 to 18 carbon atoms, an allyl or methallyl ester of an acid having 2 to 18 carbon atoms, an acrylate or methacrylate of a saturated alcohol having 1 to 18 carbon atoms, an alkyl vinyl ether, the alkyl radical of which contains 2 to 18 carbon atoms, an olefine having 4 to 18 carbon atoms, a heterocyclic vinyl derivative, a dialkyl or N,N-dialkylaminoalkyl maleate, the alkyl radicals of which have 1 to 3 carbon atoms, or an unsaturated acid anhydride.

(12) Quaternary polymers of vinylpyrrolidone and vinylimidazole, such as, for example, Luviquat FC 905 marketed by Messrs. BASF.

(13) Cationic silicone polymers, for example those described in European Patent Application Nos. 17,121 and 17,122, in U.S. Pat. No. 4,185,087, in Japanese Patent Application No. 80/66,506 and in Austrian Patent Application No. 71/01,171, or those mentioned in the CTFA dictionary under the name AMODIMETHICONE, such as the product marketed as a mixture with other ingredients under the name of the cationic emulsion "Dow Corning 929".

Other cationic polymers which can be used are polyalkylene-imines, in particular polyethyleneimines, polymers containing vinylpyridine or vinylpyridinium units in the chain, condensates of polyamines and epichlorohydrin, quaternary polyureylenes and derivatives of chitin.

The carboxyl groups are introduced into the anionic polymers by unsaturated monocarboxylic or dicarboxylic acids represented, in particular, by the formula:

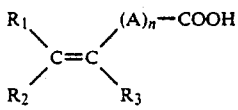

in which n represents 0 or an integer from 1 to 10, A represents a methylene group which is optionally bonded to the carbon atom of the unsaturated group, or to the adjacent methylene group if n is greater than 1, via a heteroatom, such as oxygen or sulphur, $R_1$ represents a hydrogen atom or a phenyl or benzyl grouping, $R_2$ represents a hydrogen atom or a lower alkyl or carboxyl group and $R_3$ represents a hydrogen atom or a lower alkyl, $-CH_2-COOH$, phenyl or benzyl group.

In the abovementioned formula, a lower alkyl radical preferably represents a group having 1 to 4 carbon atoms, in particular methyl or ethyl.

The preferred anionic polymers used according to the invention are in particular:

homopolymers or copolymers of acrylic or methacrylic acid or their salts, in particular products marketed under the names VERSICOL E or K by ALLIED COLLOID or ULTRAHOLD 8 by CIBA GEIGY, copolymers of acrylic acid and acrylamide marketed in the form of their sodium salt under the names RETEN 421, 423 or 425 by HERCULES, sodium polymethacrylate marketed under the name DARVAN No. 7 by Van der Bilt, and the sodium salts of polyhydroxycarboxylic acids marketed under the name HYDAGEN F by HENKEL;

copolymers of the abovementioned acids with a monoethylenic monomer, such as ethylene, vinylbenzene, vinyl esters, allyl esters and esters of acrylic or methacrylic acid, optionally grafted onto a polyalkylene glycol, such as polyethylene glycol, and optionally crosslinked. Such polymers are described, in particular, in French Pat. No. 1,222,944 and German Patent Application No. 2,330,956; the copolymers of this type containing an optionally N-alkylated and/or -hydroxyalkylated acrylamide unit in their chain, such as those described, in particular, in Luxemburg Pat. Nos. 75,370 and 75,371;

copolymers derived from crotonic acid, such as those containing vinyl acetate or propionate units in their chain and optionally other monomers, such as allyl or methallyl esters, vinyl ether or the vinyl ester of a carboxylic acid of a saturated long-chain hydrocarbon, such as those containing at least 5 carbon atoms, or a vinyl, allyl or methallyl ester of a carboxylic or cyclic acid, these polymers being optionally grafted and crosslinked. Such polymers are described, inter alia, in French Pat. Nos. 1,222,944, 1,580,545, 2,265,782, 2,265,781, 1,564,110 and 2,439,798. The commercial products included in this class are the resins 28-29-30, 26-13-14 and 28-13-10 marketed by National Starch.

Polymers derived from maleic, fumaric or itaconic acid or anhydride with vinyl esters, vinyl ethers, vinyl halides, phenylvinyl derivatives and acrylic acid and it esters; these polymers may be esterified. Such polymers are described, in particular, in U.S. Pat. Nos. 2,047,398, 2,723,248 and 2,102,113 and British Pat. No. 839,805. There may be mentioned, in particular, polymers marketed under the names GANTREZ AN, S or ES by General Anilin, or EMA 1325 or 91 by MONSANTO. Polymers which can also be included in this class are copolymers of maleic, citraconic or itaconic anhydride and an allyl or methallyl ester, optionally containing an acrylamide or methacrylamide grouping in their chain and monoesterified or monoamidified, as described in French Pat. Nos. 2,350,834 and 2,357,241 of the Applicant Company.

Polyacrylamides containing carboxylate groups, such as those marketed by American Cyanamid under the name CYANAMER A 370.

Polymers with a sulphonic acid group which can be used according to the invention are chosen, in particular, from:

Salts of polystyrenesulphonic acid, such as the sodium salts marketed under the name Flexan 500 and having a molecular weight of about 500,000, or under the name Flexan 130 and having a molecular weight of about 100,000, by National Starch. Such compounds are described in particular, in French Pat. No. 2,198,719.

Alkali metal or alkaline earth metal salts of sulphonic acids derived from lignin, and, more particularly, calcium or sodium lignosulphonates, such as the product marketed under the name Marasperse C-21 by American Can Co, and those $C_{10}$–$C_{14}$ products marketed by Avébéne, Polyacrylamide-sulphonic acid salts, such as those mentioned in U.S. Pat. No. 4,128,631, and more particularly the polyacrylamido-ethylpropanesulphonic acid marketed under the name COSMEDIA POLYMER HSP 1180 by HENKEL.

Polymers containing alkylnaphthalenesulphonic acid salt units, such as the sodium salt, marketed under the name Darvan No. 1 by Van der Bilt.

Polymers containing in their chain at least one vinylsulphonic acid unit, such as, more particularly, polyvinylsulphonates having a molecular weight of from 1,000 to 100,000, and especially their sodium, potassium, calcium and ammonium salts, and amine salts, such as alkylamine and alkanolamine salts, as well as copolymers containing at least vinylsulphonic acid groups with one or more cosmetically acceptable comonomers, such as unsaturated acids chosen from acrylic and methacrylic acid and their esters, amides, such as substituted or unsubstituted acrylamide or methacrylamide, vinyl esters, vinyl ethers and vinylpyrrolidone. These polymers are described, more particularly, in French Pat. No. 2,238,474 and U.S. Pat. Nos. 2,961,431 and 4,138,477.

It is also possible to use, according to the invention, amphoteric polymers instead of the cationic polymers or instead of the anionic polymers. In this case, amphoteric polymers are necessarily used either with an anionic polymer, if the amphoteric polymer replaces the cationic polymer, or with a cationic polymer, if the amphoteric polymer replaces the anionic polymer.

The amphoteric polymers generally consist of units A and B distributed randomly in the polymer chain, where A represents a unit derived from a monomer containing at least one basic nitrogen atom and B represents a unit derived from an acid monomer containing one or more carboxylic acid or sulphonic acid groups, or A and B may represent groups derived from Zwitter-ion monomers of carboxybetaine; A and B may also represent a cationic polymer chain containing secondary, tertiary or quaternary amine groups in which at least one of the amine groups carries a carboxylic acid or sulphonic acid group bonded via a hydrocarbon radical, or A and B form part of a polymer chain with ethylene-$\alpha,\beta$-dicarboxylic acid units, in which one of the carboxyl groups has been reacted with a polyamine containing one or more primary, secondary or tertiary amine groups.

These polymers are described, in particular, in U.S. Pat. No. 3,836,537 and French Pat. No. 1,400,366 and in French Patent Application No. 79/29,319. It is also possible to use amphoteric polymers of dialkylaminoalkyl meth(acrylate) or betainised meth(acrylamide) containing the units:

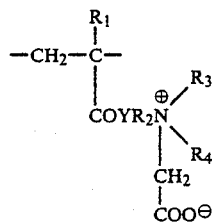

in which $R_1$ represents a hydrogen atom or a methyl group, $R_2$ represents an alkylene group with 1 to 4 carbon atoms, Y represents O or NH and $R_3$ and $R_4$ independently of one another represent hydrogen or alkyl having 1 to 4 carbon atoms, and copolymers with acrylic or methacrylic acid esters containing alkyl radicals having 4 to 24 carbon atoms and acrylic or methacrylic acid esters containing alkyl radicals having 1 to 3 carbon atoms and optionally other monomers, such as N-vinylpyrrolidone, acrylamide, hydroxyethylpropyl acrylate or methacrylate, acrylonitrile, styrene, chlorostyrene, vinyltoluene, vinyl acetate and the like, which are known per se.

Of the cationic surface-active agents which may be used, by themselves or as a mixture, in the hair compositions according to the invention, there may be mentioned in particular: salts of fatty amines, such as alkylamine acetates, quaternary ammonium salts, such as alkyldimethylbenzylammonium, alkyltrimethylammonium, dialkyldimethylammonium and alkyldimethylhydroxyethyltrimethylammonium chlorides and bromides in which the alkyl radicals preferably have between 1 and 22 carbon atoms, quaternary halides of gluconamide, such as those described in U.S. Pat. No. 3,766,267, quaternary halides of the amide of the oil of mink, such as those described in U.S. Pat. No. 4,012,398, quaternary derivatives of fatty haloalkanoates of dialkylaminopropylamide, such as those described in U.S. Pat. No. 4,038,294, quaternary ammonium derivatives of the fatty acids of lanolin, such as those described in U.S. Pat. No. 4,069,347, alkylpyridinium salts and derivatives of imidazoline.

Compounds having a cationic character, such as amine oxides, such as alkyldimethylamine oxides or alkylaminoethyldimethylamine oxides, may also be mentioned.

Of the anionic surface-active agents, which can be used by themselves or as a mixture, there may be mentioned in particular: alkali metal salts, ammonium salts, amine salts and aminoalcohol salts of the following compounds:

alkyl-sulphates, alkyl ether-sulphates, alkylamide sulphates and ether-sulphates, alkylarylpolyethersulphates and monoglyceride sulphates, alkylsulphonates, alkylamide-sulphonates, alkylarylsulphonates, olefin-sulphonates and paraffin-sulphonates, alkylsulphosuccinates, alkyl ether-sulphosuccinates and alkylamide-sulphosuccinates, alkylsulphosuccinamates, alkylsulphoacetates and alkylpolyglycerol carboxylates, alkyl phosphates and alkyl ether-phosphates and alkylsarcosinates, alkylpolypeptidates, alkylamidopolypeptidates, alkylisethionates and alkyltaurates.

The alkyl radical of all of these compounds is most frequently a linear chain with 12 to 18 carbon atoms.

Fatty acids, such as oleic acid, ricinoleic acid, palmitic acid and stearic acid, and the acids of coconut oil or hydrogenated coconut oil.

The following may also be mentioned:

acyl lactates, the alkyl radical containing 8 to 20 carbon atoms;

carboxylic acids of polyglycol ethers, corresponding to the formula:

$$Alk-(OCH_2-CH_2)_n-OCH_2-COOH$$

in the form of bases or salts where the substituent Alk contains a linear chain having 12 to 18 carbon atoms, and where n is an integer from 5 to 15.

Of the anionic surface-active agents, those which are more particularly preferred are: the lauryl-sulphate of sodium, ammonium or triethanolamine, the lauryl ether-sulphate of sodium, oxyethyleneated with 2.2 mol of ethylene oxide, the triethanolamine salt of lauroyl-keratinic acid, the triethanolamine salt of the condensation product of coconut oil acids and hydrolysis products of animal proteins, and products of the formula:

$$R-OCH_2-CH_2)_x-OCH_2-COOH$$

in which R represents an alkyl group, in general a $C_{12}-C_{14}$-alkyl group, and x is from 6 to 10.

Of the non-ionic surface-active agents which may be used by themselves or as a mixture, there may be mentioned in particular: polyethoxylated, polypropoxylated or polyglycerolated alcohols, alkylphenols and fatty acids with a linear fatty chain containing 8 to 18 carbon atoms. Compounds which may also be mentioned are copolymers of ethylene oxide and propylene oxide, condensates of ethylene oxide and propylene oxide with fatty alcohols, polyethoxylated fatty amides, polyethoxylated fatty amines, ethanolamides, fatty acid glycol esters, oxyethyleneated or non-oxyethyleneated fatty acid sorbitan esters, fatty acid esters of sucrose, fatty acid polyethylene glycol esters, phosphorus triesters, fatty acid esters of glucose derivatives, alkylglucosides and glucoside alkyl ethers.

Other compounds included in this class are: condensation products of a monoalcohol, a diol, an alkylphenol, an amide or a diglycolamide and glycidol, such as, for example, compounds corresponding to the formula:

$$R_4-CHOH-CH_2-O-(CH_2-CHOH-CH_2-O)_pH$$

in which $R_4$ represents an aliphatic, cycloaliphatic or araliphatic group having preferably from 7 to 21 carbon atoms, and mixtures thereof, it being possible for the aliphatic chains to contain ether, thioether or hydroxymethylene groups, and where p is from 1 to 10 inclusive; such as those described in French Pat. No. 2,091,516.

Compounds corresponding to the formula:

$$R_5O(C_2H_3O-(CH_2OH))_qH$$

in which $R_5$ represents an alkyl, alkenyl or alkylaryl group and q is a statistical value of from 1 to 10 inclusive, such as those described in French Pat. No. 1,477,048.

Compounds corresponding to the formula:

$$R_6CONH-CH_2-CH_2-O-CH_2-CH_2-O-(CH_2CHOH-CH_2-O)_rH$$

in which $R_6$ represents one or a mixture of linear or branched, saturated or unsaturated aliphatic groups which can optionally contain one or more hydroxyl groups have from 8 to 30 carbon atoms and are of natural or synthetic origin, and r represents an integer or a decimal number from 1 to 5 and designates the average degree of condensation, such as those described in French Pat. No. 2,328,763.

Of these non-ionic surface-active agents, those which are more particularly preferred correspond to the formula:

$$R_4-CHOH-CH_2-O(CH_2-CHOH-CH_2-O)_pH$$

where $R_4$ represents a mixture of alkyl groups having 9 to 12 carbon atoms and p has a statistical value of 3.5.

$$R_5O-(C_2H_3O-(CH_2OH))_qH$$

where $R_5$ represents $C_{12}H_{25}$ and q has a statistical value of 4 to 5.

$$R_6-CONH-CH_2-CH_2-O-CH_2-CH_2-O-(CH_2CHOH-CH_2)_rH$$

where $R_6$ represents a mixture of groups derived from lauric acid, myristic acid, oleic acid and coconut oil acid and r has a statistical value of 3 to 4.

The preferred oxyethyleneated or polyglycerolated fatty alcohols are oleyl alcohol oxyethyleneated with 10 mol of ethylene oxide, lauryl alcohol oxyethyleneated with 12 mol of ethylene oxide, nonylphenol oxyethyleneated with 9 mol of ethylene oxide, oleyl alcohol polyglycerolated with 4 mol of glycerol and sorbitan monolaurate polyoxyethyleneated with 20 mol of ethylene oxide.

Of the amphoteric surface-active agents which can be used, there may be mentioned more particularly alkylamino-mono- and -di-propionates, betaines, such as N-alkylbetaines, N-alkylsulphobetaines and N-alkylamidobetaines, cycloimidinium compounds, such as alkylimidazolines, and asparagine derivatives.

The alkyl group in these surface-active agents preferably is a group having from 1 to 22 carbon atoms.

These surface-active agents are in general included in amounts varying from 0.1 to 30%, preferably from 0.2 to 20%.

The hair compositions used for conditioning hair according to the invention are essentially used as rinsing lotions.

These lotions are solutions which are applied before or after colouring, before or after bleaching, before or after permanent waving, before or after shampooing or between two shampooing stages, in order to achieve a conditioning effect on the hair, and the hair is rinsed after a residence time. This residence time is in general from 1 minute to 30 minutes and preferably from 2 to 15 minutes.

The pH of these so-called rinsing lotions suitably varies from 2 to 10, and is preferably from 3 to 8.

These lotions are in general in the form of a thickened liquid, a gel or a cream and may contain another thickener, whilst remaining homogeneous, for modification of the appearance and feel, such as guar gum or derivatives thereof, as well as any other ingredient usually employed in cosmetics, such as perfumes, colorants, preservatives, sequestering agents and emollients.

The process for conditioning hair, which is an object of the invention, comprises applying at least one of the compositions defined above to the hair, keeping these compositions in contact with the hair for a period sufficient for impregnation of the hair, preferably for from 1 to 30 minutes, and rinsing the hair with water.

The Examples which follow further illustrate the present invention; "AS", as used herein, stands for "Active Substance".

EXAMPLE 1

The following composition is prepared:

| | |
|---|---|
| Gafquat 755 | 0.7 g of AS |
| Sodium polyvinyl sulphonate | 1.8 g of AS |
| Dialkyldimethylammonium chloride (alkyl = derivatives of tallow fatty acids) | 0.5 g of AS |
| Actigum CX 9 | 0.5 g |
| Water q.s.p. | 100 g |

This composition is in the form of a thickened lotion. It is applied to hair and left for about 10 minutes, and the hair is then rinsed.

The hair becomes untangled very easily and, after drying, it has bounce and body.

Examples 2 to 18 which follow are prepared in the same manner as the composition of Example 1.

| Example No. | POLYMER CATIONIC | AS % g | ANIONIC | AS % g | SURFACE-ACTIVE AGENT | AS % g | ELECTROLYTE | % g | XANTHAN GUM | % g | GUAR GUM | % g |
|---|---|---|---|---|---|---|---|---|---|---|---|---|
| 2 | JR 400 | 1.0 | Hydagen F Gantrez ES 425 | 1.3 0.7 | Ammonyx 4002 | 0.6 | NaCl | 4 | Actigum CX 9 | 0.4 | | |
| 3 | Jaguar C 13 S | 0.5 | Darvan No. 7 | 1.25 | | | NaCl | 4 | KELTROL | 0.5 | | |
| 4 | Condensate of epichlorohydrin with the condensate of adipic acid and diethylenetriamine according to Example Ia of French Patent 2,252,840 | 1.4 | Versicol E 5 | 2.1 | | | | | KELTROL | 0.4 | | |
| 5 | Condensate of epichlorohydrin with the condensate of adipic acid and diethylenetriamine | 1.4 | Versicol E 5 | 2.1 | | | | | KELTROL | 0.62 | | |
| 6 | Gafquat 755 | 0.7 | Sodium polyvinylsulphonate | 1.0 | Dialkyldimethylammonium chloride* | 0.8 | NaCl | 4 | KELTROL | 0.25 | | |
| 7 | Gafquat 755 | 0.7 | Sodium polyvinylsulphonate | 1.0 | Dialkyldimethylammonium chloride* | 0.8 | NaCl | 4 | KELTROL | 0.37 | | |

-continued

| Example No. | POLYMER CATIONIC | AS % g | ANIONIC | AS % g | SURFACE-ACTIVE AGENT | AS % g | ELECTROLYTE | % g | XANTHAN GUM | % g | GUAR GUM | % g |
|---|---|---|---|---|---|---|---|---|---|---|---|---|
| 8 | Merquat 550 | 1.8 | Hydagen F | 2.5 | | | NaCl | 4 | RHODOPOL 23 C | 0.5 | | |
| 9 | Delsette 101 | 1.2 | Gantrez ES 425 | 1.8 | Dialkyldi-methyl-ammonium chloride* | 0.3 | NaCl | 4 | RHODOPOL 23 C | 0.4 | | |
| 10 | Catamer Q | 0.8 | Cosmedia polymer HSP 1180 | 0.84 | | | NaCl | 4 | Deuteron XG | 0.5 | | |
| 11 | JR 400 | 0.7 | Hydagen F Gantrez ES 425 | 1.0 0.55 | Ammonyx 4002 | 0.45 | NaCl | 3 | Actigum CX9 | 0.4 | Jaguar CM HP | 0.4 |
| 12 | Condensate of piperazine and epichlorohydrin according to Example 1 of French Patent 2,162,025 | 0.6 | Cosmedia Polymer HSP 1180 | 1.5 | Ammonyx 4002 | 0.6 | NaCl | 4 | Actigum CX9 | 0.4 | Jaguar HP 60 | 0.4 |
| 13 | Cartaretine F$_4$ | 1.0 | Flexan 500 | 3.0 | Dialkyldi-methyl-ammonium chloride* | 0.5 | NaCl | 4 | Deuteron XG | 0.3 | Guar gum 10 W | 0.3 |
| 14 | Cartaretine F$_4$ | 1.0 | Flexan 500 | 2.0 | | | NaCl | 4 | Deuteron XG Rhodopol 23 C | 0.3 0.3 | Guar gum 10 W | 0.3 |
| 15 | Luviquat FC 905 | 1.5 | Gantrez ES 425 | 2.0 | Ammonyx 4002 | 0.4 | NaCl | 4 | Keltrol | 0.45 | Guar gum 10 W | 0.45 |
| 16 | Luviquat FC 905 | 1.4 | Gantrez ES 425 | 3.6 | Ammonyx 4002 | 0.4 | NaCl | 4 | Keltrol | 0.8 | Guar gum 10 W | 0.8 |
| 17 | Dow Corning 929 | 1.4 | Hydagen F | 2.0 | Dialkyldi-methyl-ammonium chloride* | 0.6 | NaCl | 4 | Rhodopol 23 C | 0.25 | Jaguar HP 60 | 0.25 |
| 18 | Dow Corning 929 | 0.8 | Hydagen F | 2.0 | Triton CG 110 and dialkyl-dimethyl-ammonium chloride* | 5.0 0.5 | NaCl | 4 | Rhodopol 23 C | 0.4 | Jaguar CMHP | 0.4 |

*alkyl designates a tallow chain

The compositions of Examples 2, 4, 5, 6, 7, 10, 12, 13 and 15 are in the form of a thickened lotion. The compositions of Examples 3, 8, 9, 11, 14, 16, 17 and 18 are in the form of a fluid gel.

As indicated above, these compositions are applied to hair and left in contact therewith for a few minutes to 30 minutes, preferably 2 to 10 minutes. Rinsing is then carried out.

In the various cases, the hair untangles easily and, after drying, has bounce and body.

In the various examples above, water was in each case added in an amount sufficient to give 100 g, and perfumes and colorants were in each added in order to improve the presentation of these compositions.

EXAMPLE 19

The following composition is prepared:
Cationic polymer consisting of recurring units:

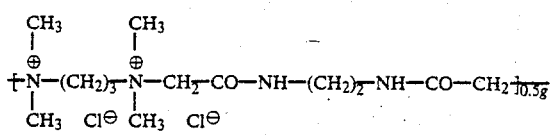

prepared according to French Pat. No. 2,413,907.

| | |
|---|---|
| Modified polyacrylamide with anionic character, marketed under the name Cyanamer A 370 by AMERICAN CYANAMID | 1 g |
| Xanthan gum marketed under the name Actigum CX 9 by CECA | 0.25 g AS |
| Surface-active agent of the formula: R—CHOH—CH$_2$—O—(CH$_2$CHOH—CH$_2$—O)$_n$—H where R is a mixture of C$_9$-C$_{12}$-alkyl groups and n is an average statistical value of about 3.5 prepared according to French Patent No. 2,091,516 | 10 g of AS |
| Sodium chloride | 4 g |
| The pH is 6 and is adjusted with hydrochloric acid | |
| Water q.s.p. | 100 g |

This composition is used as a shampoo.

EXAMPLE 20

The following composition is prepared:

| | |
|---|---|
| Polycondensate of adipic acid and diethyl- | 0.5 g of AS | enetriamine crosslinked by a crosslinking
agent of the formula:

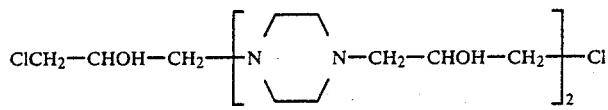

prepared according to French Patent
2,368,508.

| | |
|---|---|
| Sodium polyalkylnaphthalenesulphonate marketed under the name Darvan No. 2 by VAN DER BILT | 0.6 g of AS |
| Xanthan gum marketed under the name Rhodopol 23 by RHONE-POULENC | 0.3 g of AS |
| Sodium chloride | 3 g |
| Lauryl ether-sulphate of sodium and magnesium marketed as 30% of AS under the name Texapon ASV by HENKEL | 10 g of AS |
| pH = 7.9, adjusted with hydrochloric acid Water q.s.p. | 100 g |

This composition is used as a shampoo.

EXAMPLE 21

The following composition is prepared:

| | |
|---|---|
| Polycondensate of adipic acid and diethyl- enetriamine crosslinked by a crosslinking agent of the formula: | 1 g of AS |

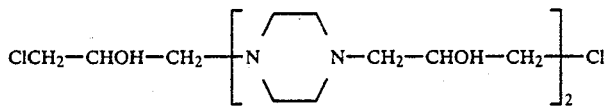

prepared according to French Patent
2,368,508.

| | |
|---|---|
| Terpolymer of vinyl acetate/crotonic acid/ vinyl neodecanoate marketed under the name Resin 28.29.30, grade E by Messrs. National Starch | 0.5 g of AS |
| Xanthan gum marketed under the name Keltrol by KELCO | 0.1 g of AS |
| Potassium salt of the condensate of coco- nut oil and collagen polypeptide marketed as 30% strength AS under the name LAMEPON S by GRUNAU | 10 g of AS |
| Sodium chloride | 4 g |
| pH = 7.5, with sodium hydroxide Water q.s.p. | 100 g |

This composition is used as a shampoo.

EXAMPLE 22

The following composition is prepared:

| | |
|---|---|
| Polycondensate of adipic acid and diethylene- triamine crosslinked by a crosslinking agent of the formula: | 0.5 g of AS |

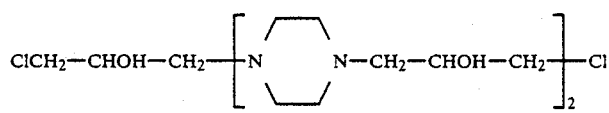

prepared according to French Patent
2,368,508.

| | |
|---|---|
| Copolymer of vinyl acetate and crotonic acid marketed under the name RESYN 281310 by NATIONAL STARCH | 0.5 g of AS |
| Xanthan gum marketed under the name Keltrol by KELCO | 0.1 g of AS |
| Sodium chloride | 4 g |
| Non-ionic hydroxypropyl-guar gum marketed under the name Jaguar HP 60 by MEYHALL | 1 g of AS |
| Surface-active agent of the formula: $R-CHOH-CH_2-O-(CH_2-CHOH-CH_2-O)_n-H$ where R = a mixture of $C_9-C_{12}$—alkyl radicals | 1 g of AS |

| | |
|---|---|
| and n = an average statistical value of about 3.5, prepared according to French Patent No. 2,091,516 | |
| Sodium chloride | 4 g |
| pH = 7.9, adjusted with hydrochloric acid Water q.s.p. | 100 g |

This composition is applied to the hair after shampooing and the hair is then rinsed with water.

EXAMPLE 23

The following composition is prepared:

| | |
|---|---|
| Polycondensate of adipic acid and diethylenetriamine, crosslinked with a crosslinking agent of the formula: | 1 g of AS |

prepared according to French Patent 2,368,508.

| | |
|---|---|
| Calcium salt of polysulphonated lignin, marketed under the name Marasperse C 21 by AMERICAN CAN COMPANY | 0.5 g of AS |
| Modified polyacrylamide with anionic character marketed under the name Cyanamer A 370 by AMERICAN CYANAMID | 0.1 g of AS |
| Xanthan gum marketed under the name Rhodopol 23 by RHONE-POULENC | 0.8 g of AS |
| Sodium chloride | 4 g |
| Trideceth-7 carboxylic acid marketed as 90% strength AS under the name Sandopan DTC acid by SANDOZ | 0.7 g of AS |
| pH = 8, adjusted with hydrochloric acid Water q.s.p. | 100 g |

This composition is applied to hair after shampooing and the hair is then rinsed.

EXAMPLE 24

The following composition is prepared:

| | |
|---|---|
| Cationic polymer consisting of recurring units: | 0.5 g of AS |

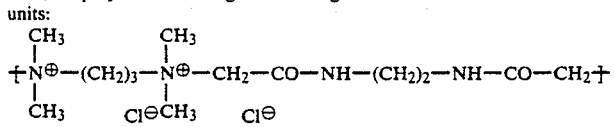

prepared according to French Patent 2,413,907.

| | |
|---|---|
| Sodium salt of a polyhydroxycarboxylic acid marketed under the name Hydagen F by HENKEL | 1.5 g of AS |
| Xanthan gum marketed under the name Rhodopol 23 by RHONE-POULENC | 0.15 g of AS |
| Sodium chloride | 3.5 g of AS |
| Non-ionic hydroxypropyl-guar gum marketed under the name Jaguar HP 60 by MEYHALL | 1.2 g of AS |
| pH = 7.25, adjusted with sodium hydroxide Water q.s.p. | 100 g |

This composition is used as an after-shampoo and is rinsed off after application.

The commercial names used in the examples represent the following products:

| | |
|---|---|
| ACTIGUM CX 9 | Xanthan gum, polysaccharide resulting from fermentation of certain sugars by microorganisms, marketed by C.E.C.A. |
| AMMONYX 4002 | Surface-active agent: stearalkonium chloride marketed by ONYX INTERNATIONAL. |
| CARTARETINE F4 | Adipic acid/dimethylaminohydroxypropyl-diethylenetriamine copolymer marketed by SANDOZ. |
| CATAMER Q | POLYQUATERNIUM 5 (C.T.F.A. nomenclature, 1982 edition), marketed by RICHARDSON. |
| COSMEDIA POLYMER HSP 1180 | Polyacrylamidoethylpropane-sulphonic acid marketed by HENKEL. |
| DARVAN No. 7 | Sodium polymethacrylate marketed by Messrs. VAN DER BILT. |

| | -continued |
|---|---|
| DELSETTE 101 | Poly-(adipic acid amide)/diethylenetriamine quaternised with epichlorohydrin, marketed by HERCULES. |
| DEUTERON XG | Anionic heteropolysaccharide xanthan gum having a molecular weight of some millions and a viscosity in 1% strength solution of 1,200 cps measured with a Brookfield LVT viscometer at 30 revolutions/minute, marketed by SCHONER G.m.b.H. |
| DOW CORNING 929 | Mixture of amodimethicone, "tallowtrimonium chloride" and nonoxynol-10 according to the CTFA Cosmetic Ingredient Dictionary, 1982 edition, marketed by DOW CORNING. |
| FLEXAN 500 | Sodium salt of polystyrenesulphonate of molecular weight of the order of 500,000, marketed by NATIONAL STARCH. |
| GAFQUAT 755 | Copolymer of quaternary polyvinylpyrrolidone having a molecular weight of 1,000,000, marketed by GENERAL ANILINE. |
| GANTREZ ES 425 | Monobutyl ester of poly-(methyl vinyl ether/maleic acid), marketed by GENERAL ANILINE. |
| 10 W GUAR GUM | Cationic guar gum marketed by Messrs. CESALPINA SpA. |
| HYDAGEN F | Polyhydroxycarboxylic acid sodium salt, marketed by HENKEL. |
| JAGUAR C 13 S | Hydroxypropyl-trimonium chloride of guar gum according to the CTFA dictionary, marketed by MEYHALL. |
| JAGUAR HP 60 | Non-ionic hydroxypropyl-guar gum, marketed by MEYHALL. |
| JAGUAR CMHP | Slightly anionic carboxymethyl-hydroxypropyl-guar gum, marketed by MEYHALL, |
| JR 400 | Polymer of hydroxyethylcellulose and epichlorohydrin quaternised with trimethylamine, marketed by UNION CARBIDE. |
| KELTROL | Xanthan gum, polysaccharide of high molecular weight. Viscosity of a 1% strength solution: 1,200–1,600 cps, measured in a Brookfield LVT viscometer at 30 revolutions/minute, marketed by KELCO, Division of MERCK & CO. |
| LUVIQUAT FC 905 | Quaternary cationic polymer having the composition: 5% of vinylpyrrolidone and 95% of vinylimidazole, marketed by BASF. |
| MERQUAT 550 | Copolymer of dimethyldiallylammonium chloride and acrylamide of molecular weight > 500,000, marketed by MERCK. |
| RESIN 28.29.30 | Terpolymer of vinyl acetate crotonic acid/vinyl neodecanoate, marketed by NATIONAL STARCH. |
| RHODOPOL 23 C | Xanthan gum, polysaccharide of high molecular weight obtained by fermentation of sugars by means of a microorganism of the Xanthomonas genus, marketed by RHONE-POULENC, viscosity of an aqueous 0.3% strength solution = 450 ± 50 cps, measured in a Brookfield LVT viscometer at 30 revolutions/minute. |
| VERSICOL E5 | Mixture of homopolymers and copolymers of acrylic acid having a viscosity of 16 cps in 25% strength solution and a molecular weight of about 3,500, marketed by ALLIED COLLOIDS. |
| TRITON CG 110 | Glucoside alkyl ether of the formula: 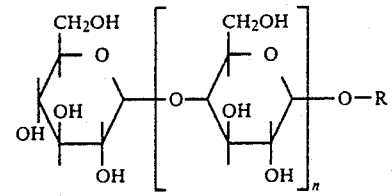 in which R represents a $C_8$-$C_{10}$ group and n = 0, 1, 2, 3 or 4, marketed by SEPPIC. |

I claim:

1. A composition suitable for application to the hair which is in the form of a thickened, stable and homogeneous lotion containing either at least one cationic polymer and at least one anionic or amphoteric polymer or at least one anionic polymer and at least one cationic or amphoteric polymer and at least one xanthan gum.

2. A composition according to claim 1 in which the xanthan gum has a molecular weight of from 1 million to 50 million and a viscosity in an aqueous 1% strength solution of from 850 to 1,600 cps.

3. A composition according to claim 1 in which the xanthan gum is present in an amount of 0.05 to 5% by weight based on the total weight of the composition.

4. A composition according to claim 3 in which the xanthan gum is present in an amount of 0.1 to 1% by weight based on the total weight of the composition.

5. A composition according to claim 1 in which the cationic polymer has a molecular weight of from 500 to 3,000,000 and the anionic polymer has a molecular weight of from 500 to 3,000,000.

6. A composition according to claim 1 in which the cationic polymer is a polymer of the polyamine, polyamino-polyamide or quaternary polyammonium type, the amino or ammonium group forming part of the polymer chain or being bonded thereto.

7. A composition according to claim 1 in which the anionic polymer is a polymer containing one or more carboxylic acid or sulphonic acid groups.

8. A composition according to claim 7 in which the polymer with a carboxylic acid group is derived from an unsaturated monocarboxylic or dicarboxylic acid represented by the formula:

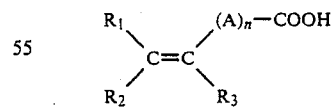

in which n represents 0 or an integer from 1 to 10, A represents a methylene group which is optionally bonded to the carbon atom of the unsaturated group, or to the adjacent methylene group if n is greater than 1, via a heteroatom, $R_1$ represents a hydrogen atom or a phenyl or benzyl group, $R_2$ represents a hydrogen atom or a lower alkyl or carboxyl group and $R_3$ represents a hydrogen atom or a lower alkyl, —$CH_2$—COOH, phenyl or benzyl group, or the polymer with a sulphonic acid group is chosen from:

a salt of a polystyrene-sulphonic acid,
an alkali metal or alkaline earth metal salt of a sulphonic acid derived from lignin,
a salt of a polyacrylamide-sulphonic acid,
a polymer containing alkylnaphthalenesulphonic acid salt units and
a polymer containing vinylsulphonic acid units.

9. A composition according to claim 5 in which the cationic polymer is chosen from:
   (1) quaternised or non-quaternised copolymers of vinylpyrrolidone and dialkylaminoalkyl acrylate or methacrylate,
   (2) cellulose ether derivatives which contain quaternary ammonium groups, and quaternary cellulose derivatives,
   (3) cationic polysaccharides,
   (4) cationic polymers chosen from the polymers containing units of the formula —A—Z—A—Z— (I) in which A represents a group containing two amine functions and Z represents the symbol B or B'; and B and B' are identical or different and represent a linear or branched alkylene group which is unsubstituted or substituted by hydroxyl groups and can also contain oxygen, nitrogen and/or sulphur atoms and 1 to 3 aromatic and/or heterocyclic rings; polymers of the formula:
   —A—$Z_1$—A—$Z_1$ (II) in which A has the same meaning as above and $Z_1$ represents the symbol $B_1$ or $B'_1$, at least one of the symbols $Z_1$ signifying $B'_1$, $B_1$ represents a linear or branched alkylene or hydroxyalkylene group, and $B'_1$ is a linear or branched alkylene group which is unsubstituted or substituted by one or more hydroxyl groups and interrupted by one or more nitrogen atoms, the nitrogen atom being substituted by an alkyl chain optionally interrupted by an oxygen atom and optionally containing one or more hydroxyl functions; and quaternary ammonium salts and oxidation products of polymers of the formula (I) or (II),
   (5) polyaminopolyamides,
   (6) crosslinked polyaminopolyamides chosen from:
   (a) optionally alkylated crosslinked polyaminopolyamides obtained by crosslinking a polyaminopolyamide prepared by polycondensation of an acid compound with a polyamine, with a crosslinking agent chosen from epihalohydrins, diepoxides, dianhydrides, unsaturated anhydrides and bisunsaturated derivatives, the crosslinking agent being used in amounts of from 0.025 to 0.35 mol per amine grouping of the polyaminopolyamide;
   (b) water-soluble crosslinked polyaminopolyamides obtained by crosslinking a polyaminopolyamide defined above with a crosslinking agent chosen from:
   I—bishalohydrins, bis-azetidines, bis-haloacyldiamines and alkyl bis-halides,
   II—oligomers obtained by reacting a compound of group I or epihalohydrins, diepoxides or bis-unsaturated derivatives with a bifunctional compound which is reactive towards these compounds,
   III—the quaternisation product of a compound of group I and oligomers of group II containing tertiary amine groupings which can be completely or partly alkylated with an alkylating agent, crosslinking being carried out by means of 0.025 to 0.35 mol of crosslinking agent per amine grouping of the polyaminopolyamide,
   (7) polyaminopolyamide derivatives resulting from the condensation of a polyalkylene-polyamine with a polycarboxylic acid, followed by alkylation with bifunctional agents,
   (8) polymers obtained by reacting a polyalkylene-polyamine containing two primary amine groups and at least one secondary amine group with a dicarboxylic acid chosen from diglycolic acid and saturated aliphatic dicarboxylic acids having 3 to 8 carbon atoms, the molar ratio between the polyalkylene-polyamine and the dicarboxylic acid being from 0.8:1 to 1.4:1; the resulting polyaminopolyamide being reacted with epichlorohydrin in a ratio of mol of epichlorohydrin to secondary amine group of the polyaminopolyamide of from 0.5:1 to 1.8:1,
   (9) cyclic polymers containing, as the principal constituent of the chain, units corresponding to the formula (III) or (III')

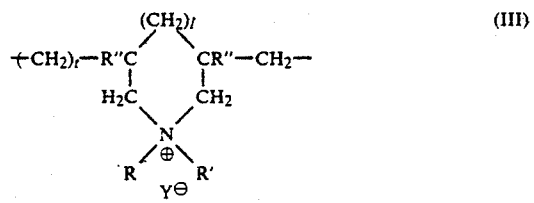

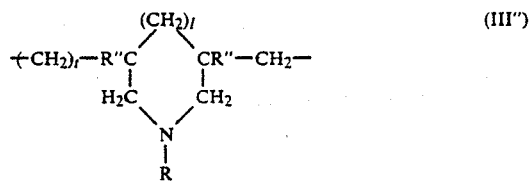

in which l and t are equal to 0 or 1 and l+t=1, R" represents hydrogen or methyl, R and R' independently of one another represent an alkyl group having 1 to 22 carbon atoms, a hydroxyalkyl group, or a lower amidoalkyl group, and where R and R' represent together with the nitrogen atom to which they are bonded, heterocyclic groups as well as copolymers containing units of the formula (III) or (III') and units derived from acrylamide or diacetone-acrylamide, and $Y^\ominus$ is an anion,
   (10) quaternary ammonium polymers of the formula:

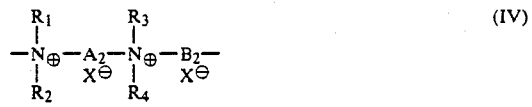

wherein $R_1$ and $R_2$, and $R_3$ and $R_4$ are identical or different and represent aliphatic, alicyclic or araliphatic groups containing at most 20 carbon atoms or lower hydroxyaliphatic groups, or $R_1$ and $R_2$ and $R_3$ and $R_4$, together or separately, represent, with the nitrogen atoms to which they are bonded, heterocyclic groups optionally containing a second hetero-atom other than nitrogen, or $R_1$, $R_2$, $R_3$ and $R_4$ represent a group:

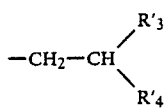

in which R′₃ represents hydrogen or lower alkyl and R′₄ represents:

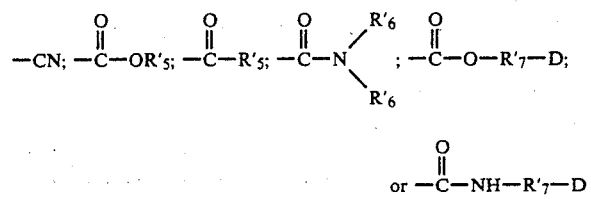

wherein R′₅ represents lower alkyl, R′₆ represents hydrogen or lower alkyl, R′₇ represents alkylene, and D represents a quaternary ammonium group, and A₂ and B₂ can represent polymethylene groups which contain 2 to 20 carbon atoms, may be linear or branched, and saturated or unsaturated and may contain, intercalated in the principal chain, one or more aromatic rings, or A₂ and R₁ and R₃ represent, with the two atoms to which they are bonded, a piperazine ring; in addition, if A₂ represents a linear or branched, saturated or unsaturated alkylene or hydroxyalkylene group, B₂ may also represent a group:

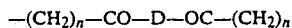

in which D represents (a) a glycol group of the formula —O—Z—O—, where Z represents a linear or branched hydrocarbon group, or a group corresponding to the formula:

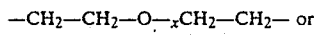

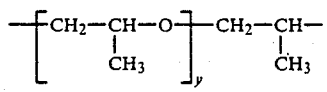

where x and y represent an integer from 1 to 4, representing a defined and single degree of polymerisation, or any number from 1 to 4, representing an average degree of polymerisation;
(b) a radical of a bis-secondary diamine;
(c) a bis-primary diamine radical of the formula:

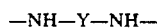

where Y represents a linear or branched hydrocarbon group or

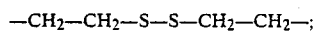

(d) a ureylene group of the formula —N-H—CO—NH—; where n is such that the molecular weight is from 1,000 to 100,000 and X⊖ represents an anion,
(11) homopolymers or copolymers derived from acrylic or methacrylic acid and containing at least one unit:

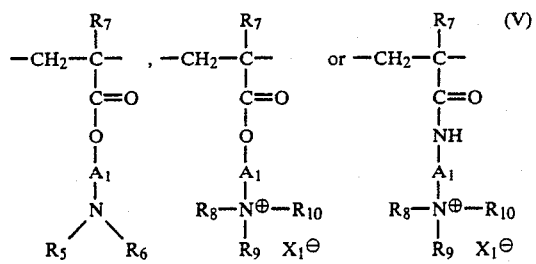

in which R₇ represents H or CH₃; A₁ represents a linear or branched alkyl group with 1 to 6 carbon atoms or a hydroxyalkyl group with 1 to 4 carbon atoms; R₈, R₉ and R₁₀ are identical or different and represent an alkyl group having 1 to 18 carbon atoms or a benzyl group; R₅ and R₆ represent H or alkyl having 1 to 6 carbon atoms; and X⊖ represents a methosulphate or halide anion,

(12) quaternary copolymers of vinylpyrrolidone and vinylimidazole,
(13) cationic silicone polymers,
(14) polyalkylene-imines,
(15) polymers containing vinylpyridine or vinylpyridinium units in the chain,
(16) condensates of polyamines and epichlorohydrin,
(17) quaternary polyureylenes and
(18) chitin derivatives.

10. A composition according to claim 1 in which the amphoteric polymer consists of units A and B distributed randomly in the polymer chain, where A represents a unit derived from a monomer containing at least one basic nitrogen atom and B represents a unit derived from an acid monomer containing or more or carboxylic acid or sulphonic acid groups, or A and B represent groups derived from Zwitter-ion monomers of carboxybetaine, or A and B may represent a cationic polymer chain containing secondary, tertiary or quaternary amine groups in which at least one of the amine groups carries a carboxylic acid or sulphonic acid group bonded via a hydrocarbon radical, or A and B form part of a polymer chain with ethylene-α,β-dicarboxylic acid units, in which one of the carboxylic acid groups has been reacted with a polyamine containing one or more primary or secondary groups.

11. A composition according to claim 1 in which the cationic and anionic polymers are present in amounts of from 0.01 to 10% by weight.

12. A composition according to claim 11 in which the cationic and anionic polymers are present in amounts of from 0.05 to 5% by weight.

13. A composition according to claim 11 in which the weight ratio of cationic polymer to anionic polymer is from 0.1:1 to 40:1.

14. A composition according to claim 1 which also contains at least one cationic, anionic, non-ionic or amphoteric surface-active agent or mixture thereof in an amount of 0.1 to 30% by weight.

15. A composition according to claim 14 in which the at least one cationic, anionic, non-ionic or amphoteric surface-active agent or mixture thereof is present in an amount of 0.2 to 20% by weight.

16. A composition according to claim 14 which contains a non-ionic surface-active agent.

17. A composition according to claim 1 which also contains a perfume, colorant, preservative, sequestering agent and emollient, and a non-ionic polymer, acidifying agent or alkalising agent.

18. A composition according to claim 1 which also contains at least one alkali metal or alkaline earth metal salt.

19. A composition according to claim 18, in which the alkali metal salt is a halide, sulphate, acetate or lactate of sodium, potassium or lithium, or the alkaline earth metal salt is a carbonate, silicate, nitrate, lactate, gluconate or pantothenate of calcium, magnesium or strontium.

20. A composition according to claim 1 which also contains guar gum.

21. A process for the treatment of hair in order to condition it, in which at least one composition as claimed in claim 1 is applied to the hair and, after a residence time of 1 to 30 minutes, the hair is rinsed and then dried.

* * * * *